United States Patent
Bihler (10) Patent No.: US 10,426,947 B2
(45) Date of Patent: Oct. 1, 2019

(54) IMPLANTABLE ELECTRODE WITH HOLLOW CYLINDRICAL SHEATH

(71) Applicant: BIOTRONIK SE & Co. KG, Berlin (DE)

(72) Inventor: Eckardt Bihler, Winterthur (CH)

(73) Assignee: BIOTRONIK SE & Co. KG, Berlin (DE)

( * ) Notice: Subject to any disclaimer, the term of this patent is extended or adjusted under 35 U.S.C. 154(b) by 84 days.

(21) Appl. No.: 15/359,742

(22) Filed: Nov. 23, 2016

(65) Prior Publication Data

US 2017/0165472 A1    Jun. 15, 2017

(30) Foreign Application Priority Data

Dec. 15, 2015 (DE) .......................... 10 2015 121 813

(51) Int. Cl.
*A61N 1/05* (2006.01)

(52) U.S. Cl.
CPC ...................................... *A61N 1/05* (2013.01)

(58) Field of Classification Search
CPC ........................................................ A61N 1/05
See application file for complete search history.

(56) References Cited

U.S. PATENT DOCUMENTS

| | | | |
|---|---|---|---|
| 7,239,922 B1* | 7/2007 | Boogaard | A61N 1/0551 607/116 |
| 7,630,749 B2* | 12/2009 | Squeri | A61N 1/056 600/373 |
| 8,150,533 B2* | 4/2012 | Wessman | A61N 1/05 607/116 |
| 9,393,404 B2* | 7/2016 | Decre | A61N 1/0551 |
| 2009/0125089 A1* | 5/2009 | Bischoff | A61N 1/0551 607/116 |
| 2009/0281608 A1 | 11/2009 | Foster | |
| 2010/0331934 A1 | 12/2010 | McDonald et al. | |
| 2013/0158638 A1 | 6/2013 | Zhulati et al. | |

OTHER PUBLICATIONS

German Search Report for German Case No. DE 10 2015 121 813.5, dated Jun. 30, 2016 (8 pages).

* cited by examiner

*Primary Examiner* — Eric D. Bertram
(74) *Attorney, Agent, or Firm* — Buchanan Ingersoll & Rooney PC

(57) ABSTRACT

An implantable electrode and a process to produce an implantable electrode. To make it possible to produce the implantable electrode in a simple and economical manner, a connection cable of the electrode is at least partly embedded in a sheath of the electrode and the sheath is in the shape of a hollow cylinder.

8 Claims, 5 Drawing Sheets

IMPLANTABLE ELECTRODE WITH HOLLOW CYLINDRICAL SHEATH

CROSS-REFERENCE TO RELATED APPLICATIONS

This patent application claims the benefit of and priority to co-pending German Patent Application No. DE 10 2015 121 813.5, filed on Dec. 15, 2015 in the German Patent Office, which is hereby incorporated by reference in its entirety.

TECHNICAL FIELD

The present invention relates to an implantable electrode with a sheath that extends along the longitudinal axis of the electrode and that is made of an electrically insulating material; and with at least one connection cable. The present invention further relates to a process to produce an implantable electrode.

BACKGROUND

Implantable electrodes and processes to produce them are generally known. However, if the known electrodes should have at least one and possibly even more connection cables to connect contact elements of the electrode with a device, then known electrodes require a great deal of effort and expense to produce. For instance, it takes a great deal of effort to sheath the at least one connection cable. If a ribbon cable is used to provide the connection cable, then it is flexible back and forth only in one preferred direction, and therefore it is difficult to implant.

The present invention is directed toward overcoming one or more of the above-mentioned problems.

Therefore, the present invention has the goal of providing an implantable electrode that is easily implantable, and a process to produce an implantable electrode that makes it simple and inexpensive to produce the implantable electrode.

SUMMARY

For the electrode mentioned at the beginning, this is accomplished by at least partly embedding the connection cable in the sheath and by the sheath having a hollow cylindrical shape. For the process mentioned at the beginning, this is accomplished by embedding at least one connection cable in a sheath of the electrode and by the sheath having a hollow cylindrical shape.

Embedding the connection cable in the sheath means that the connection cable no longer needs to be separately surrounded by an insulator. In particular, if the electrode has multiple connection cables, the sheath can suffice to hold the connection cables so that they are insulated. The separate insulation layers that are present in a normal multi-conductor cable to insulate the connection cables from one another are not necessary. This reduces not only the effort required to produce the electrode, but also its diameter. The hollow cylindrical shape of the sheath means that the electrode does not have any preferred direction in which it is more easily deformable than in other directions. Consequently, it is simple to push the implantable electrode through the patient's body and deform it in different directions.

The inventive solution can be further improved by various embodiments, each of which is advantageous taken by itself and can be combined with other embodiments, either in whole or in part, unless otherwise stated. These embodiments and their advantages are discussed below.

Thus, the electrode can have at least one contact element that has an electrically conductive connection, passing through the sheath material, with the connection cable. The connection between the connection cable and the contact element can be provided in the form of a so-called feedthrough. Having the connection cable make contact with the contact element through the sheath material eliminates the need for separate insulation of the feedthrough, and the feedthrough requires little space.

When the electrode is in the implanted state, the at least one contact element makes electrical contact with muscle cells, for example of the heart, or nerve endings, to allow electrical stimulation of the muscle cells or nerve endings. The at least one connection cable makes contact with the at least one contact element, in particular at a distal end of the electrode, and runs to an opposite end of the electrode, where it can be connectable, or even connected, with a medical device in such a way that a signal can be transferred.

The at least one contact element can extend at least partly or even completely around the longitudinal axis of the electrode, to make it simpler to make contact with the muscle cells or nerve endings when the electrode is implanted.

The electrode can have multiple connection cables that are at least partly or completely embedded in the sheath and that are arranged spaced apart from one another in the sheath's peripheral direction extending around the longitudinal axis. The fact that the connection cables are arranged spaced apart from one another in the peripheral direction allows them to pass through the sheath in a simple and collision-free manner. To make a further improvement in the property of the electrode that it is deformable without a preferred direction and, for example, flexible, the connection cables can be arranged to be evenly distributed around the longitudinal axis in the peripheral direction.

To allow multiple muscle areas or nerve endings to be contacted, the electrode can have multiple contact elements. Each of the contact elements can have an electrically conductive connection with one of the connection cables. In particular, each of the contact elements can have an electrically conductive connection, through the sheath material, with at least one of the connection cables.

To allow some or all of the contact elements to extend at least partly, or even completely, around the longitudinal axis of the electrode, and thus to make it simple for them to be put in contact muscle cells or nerve endings, the contact elements can be arranged spaced apart from one another along the longitudinal axis.

The electrode can have a core against which the sheath lies. It is preferable for the core to have a cylindrical or hollow cylindrical shape, and to be tubular, for example. The core can prevent the sheath from kinking if it should be bent too strongly, that is with too small a bend radius, and the resulting edges or corners of the kink making the implantation of the electrode difficult.

The sheath can be connected with the core by material bonding, for example, by fusion, allowing the sheath and core to be connected without other means, for example, glue or stitches.

The core can be made with a lumen extending continuously through the core along the longitudinal axis of the electrode, so that the electrode can be implanted, for example, with the help of a guide wire that guides the electrode during implantation. If the electrode is made without a core, the hollow cylindrical sheath can provide the lumen.

The material of the sheath can be a thermoplastic polymer, for example, a liquid crystal polymer. The core can be made, for example, of glass or also of a polymer, for example, a liquid crystal polymer, and even consist of it. The connection cable consists, for example, of gold or a gold alloy. The at least one contact element can be made of gold, a gold alloy, or a platinum-iridium alloy, for example.

The sheath is preferably at least almost ring-shaped and can have ends facing one another in the peripheral direction and in the opposite direction and jointly running parallel to the longitudinal axis.

The at least one connection cable or selected connection cable(s) or all the multiple connection cables can be aligned parallel to the longitudinal axis. Alternatively, the at least one connection cable or the multiple connection cable(s) can be spiral-shaped or helical, that is, for example, coiled, to run around the longitudinal axis. Moreover, it is possible for the at least one connection cable or selected connection cable(s) or all the multiple connection cables to be arranged to run in the sheath material in a meandering pattern, that is transverse to the longitudinal axis of the electrode, at least in sections. Moreover, the connection cables can be arranged interwoven with one another, it being possible for the connection cables to have insulating sheath material remaining between them. This can improve not only the deformability in various directions. If the sheath material is elastic along the longitudinal axis, at least the connection section of the electrode can be stretchable along the longitudinal axis due to the shape of the connection cables.

According to one embodiment of the inventive process, the sheath can have a planar shape and the at least one connection cable can be embedded in the planar sheath, the planar sheath with the at least one embedded connection cable being put into the hollow cylindrical shape. For example, the sheath can be in the form of a ribbon cable, the at least one connection cable being arranged between two electrically insulating films, in particular thermoplastic polymer films, made of a liquid crystal polymer, for example. In particular, one of the films can have the at least one connection cable on one of its sides. The at least one contact element can be on, or be put on, the side of this film opposite the connection cable. The connection cable and/or the contact element can put on the film additively or subtractively. To allow the connection cable and the contact element to be connected with one another, the feedthrough can be in the form of a so-called metallized via. A via is, for example, a metallized opening in the film connecting the two sides of the film with one another.

The film can be laid around the core with the contact element and the connection cable. Alternatively or additionally, another film can be laid on the side of the film that has the connection cable. Especially if the films are thermoplastic polymer films, the two films can be permanently connected with one another using thermal means. The sheath can then, together with the film without the contact element, be laid around the core.

In order to be able to connect the sheath with the core, the sheath can first be laid around the core, the sheath being able to nestle against the core, especially along the peripheral direction, and surround it, at least partly or even completely.

Preferably one width of the planar sheath corresponds essentially to the outer periphery of the core, so that the sheath can essentially completely surround the core, without an edge of the planar sheath overlapping the opposite edge of the planar sheath.

In order to be able to fasten the sheath and the core to one another in a simple manner, the sheath and the core can be connected with one another by material bonding. Especially if both the sheath material and the core are made of a thermoplastic polymer material, the sheath and the core can be fastened to one another in a simple manner under the effect of temperature and pressure, and fused, for example. For example, the sheath can be pressed against the core by a mold that preferably does not stick to the sheath and that has, for example, Teflon® or ceramic surfaces that come in contact with the sheath when the electrode is being produced. To be able to fasten the sheath to the core, the sheath and core can be heated to up to 350° C., for example to 200° C. These temperatures can be maintained for up to 20 minutes, for example, for at least 1 second. The material of the sheath and core can be fused together in such a heat treatment, and in this way be seamlessly, or at least almost seamlessly, connected together by material bonding.

For example, polyurethane or another polymer can be used as a liquid crystal polymer. If the core has glass or carbon fibers, these fibers can be coated with thermoplastic polymer material, to make it simple to connect the sheath with the core by material bonding.

The diameter of the electrode can lie between 200 μm and 700 μm, and be, for example, 250 μm, 400 μm, or 500 μm. The separation of the at least one connection cable to the longitudinal axis can be between 50 μm and 250 μm, and, for example, 90 μm, 165 μm, or 215 μm. If multiple connection cables are provided, they can be arranged on a ring surrounding the longitudinal axis, it being possible for the ring to have a diameter between 100 μm and 500 μm, for example, 180 μm, 330 μm, or 430 μm. The diameter of the core can lie between 100 μm and 400 μm, and be, for example, 110 μm, 260 μm, or 360 μm. If the connection cables are separated by 25 μm in the peripheral direction, the electrode can have up to 11, up to 21, or even up to 30 connection cables, for example, 27 connection cables. If the connection cables are separated by 15 μm in the peripheral direction, the electrode can have up to 19, up to 35, or even up to 50 connection cables, for example, 45 connection cables. Each of the connection cables can have an electrically conductive connection with a separate contact element. However, it can be sufficient for the electrode to have two or three connection cables and contact elements, for example, if the electrode is designed to connect a cardiac pacemaker or defibrillator with the heart.

Further embodiments, features, aspects, objects, advantages, and possible applications of the present invention could be learned from the following description, in combination with the Figures, and the appended claims.

BRIEF DESCRIPTION OF THE DRAWINGS

The present invention is explained below on the basis of sample embodiments that make reference to the drawings. The different features of these embodiments can be combined independently of one another, as has already been explained for the advantageous embodiments.

DETAILED DESCRIPTION

First, the structure and function of an inventive implantable electrode are described with reference to the sample embodiment of FIG. 1.

Figures 1, 2:
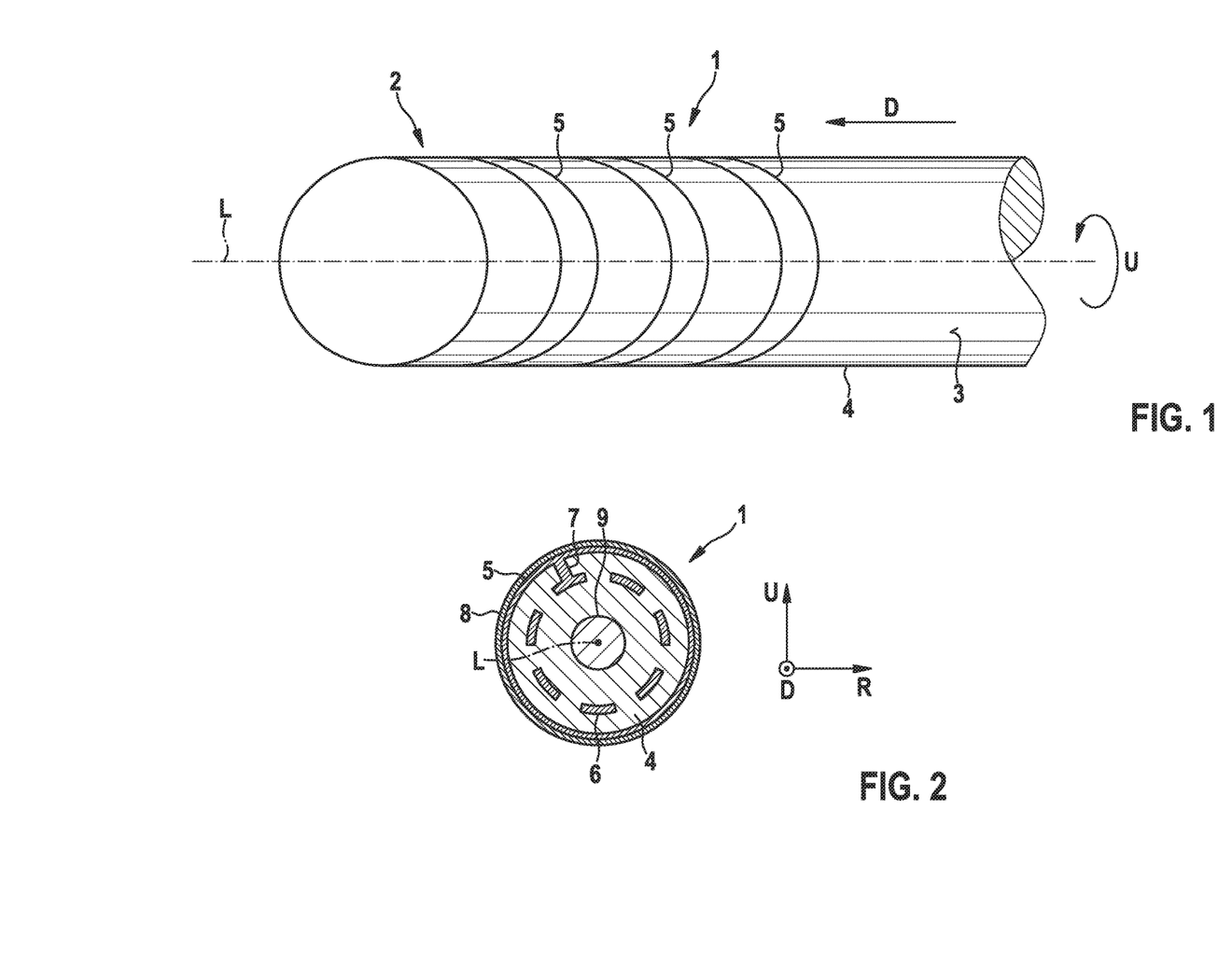
FIG. 1 is a perspective schematic representation of a sample embodiment of the inventive implantable electrode.
FIG. 2 is a schematic sectional view of another sample embodiment of the inventive implantable electrode.

FIG. 1 is a schematic perspective view of the implantable electrode 1. In particular, FIG. 1 shows a distal end 2 of the electrode 1. The distal end 2 is designed to make electrical contact with muscle cells or nerve endings, to be able to stimulate them. Alternatively, the end 2 can also be a connection end of the electrode 1 opposite the distal end of the electrode 1 and be [intended] to connect electrode 1 to a medical device, for example, a cardiac pacemaker or a defibrillator. The implantable electrode 1 has a longitudinal axis L that extends through the center of electrode 1. The implantable electrode 1 is deformable, in particular, flexible or pivotable, in all directions pointing transverse to the longitudinal axis L.

The electrode 1 is shown with an outside 3 of a sheath 4 of the electrode 1. The electrode 1 of the sample embodiment in FIG. 1 has three contact elements 5 on the sheath 4 that are accessible from outside the electrode 1. The implantable electrode 1 can also more than or fewer than three contact elements 5. For example, the electrode 1 can have one contact element 5 or more than one contact element 5, for example, two, four, five, up to 11, 19, 21, 35, 27, 30, 45, or even up to 50 contact elements 5.

The outside 3 of the sheath 4 runs parallel to the longitudinal axis L and extends in a peripheral direction U of the electrode 1 around the longitudinal axis L. The contact elements 5 extend in the peripheral direction U at least partly or even completely around the longitudinal axis L, so that it is possible to make contact with them from several or even all directions pointing toward to the longitudinal axis L. That is, the contact elements 5 can be referred to as contact rings.

The contact elements 5 are arranged spaced apart from one another in a longitudinal direction D of the electrode 1, this direction D running parallel to the longitudinal axis L and pointing toward the distal end 2. This ensures that the contact elements 5 do not make unwanted electrical contact with one another, but rather are electrically insulated from one another by sheath 4.

FIG. 2 shows a schematic sectional view of another sample embodiment of the implantable electrode 1. Elements whose form and/or function correspond to those of elements of the previous sample embodiment are labeled using the same reference numbers. For brevity, only the differences from the previous sample embodiment are discussed below.

The cutting plane runs transverse to the longitudinal axis L and through one of the connection contact elements 5 of electrode 1. Electrode 1 of the sample embodiment in FIG. 2 has multiple connection cables 6, for example, seven connection cables 6. Each of the connection cables 6 can have an electrically conductive connection with a different connection contact element. In the sample embodiment in FIG. 2, a feedthrough 7, which can also be referred to as a via, connects one of the connection cables 6 with contact element 5 through which the cutting plane extends.

The connection cables 6 are embedded in the sheath 4. The feedthrough 7 runs from the contact element 5 that is shown to one of the connection cables 6, also extending through the material of the sheath 4. In particular, the feedthrough 7 can extend, in a radial direction R running transverse to the longitudinal axis L, between the contact element 5 that is shown and the connection element 6 that has an electrically conductive connection with this contact element 5. Each of the connection cables 6 can have, with the help of another feedthrough 7, an electrically conductive connection with one of the contact elements 5.

On its outside, pointing away from the longitudinal axis L, the contact element 5 can have a metallic layer 8 that is a platinum-iridium alloy, for example.

The sheath 4 can extend around a cylindrical hollow space, which can be in the form of a lumen to hold a guide wire, for example. However, in the sample embodiment in FIG. 2, the electrode 1 is shown with a core 9 around which the sheath 4 completely extends. The core 9 itself can be in the form of a solid cylinder or hollow cylinder, for instance, it can be tubular. The sheath 4 can be fastened to the core 9 and be connected with the core 9 by material bonding, for example.

Figure 3:
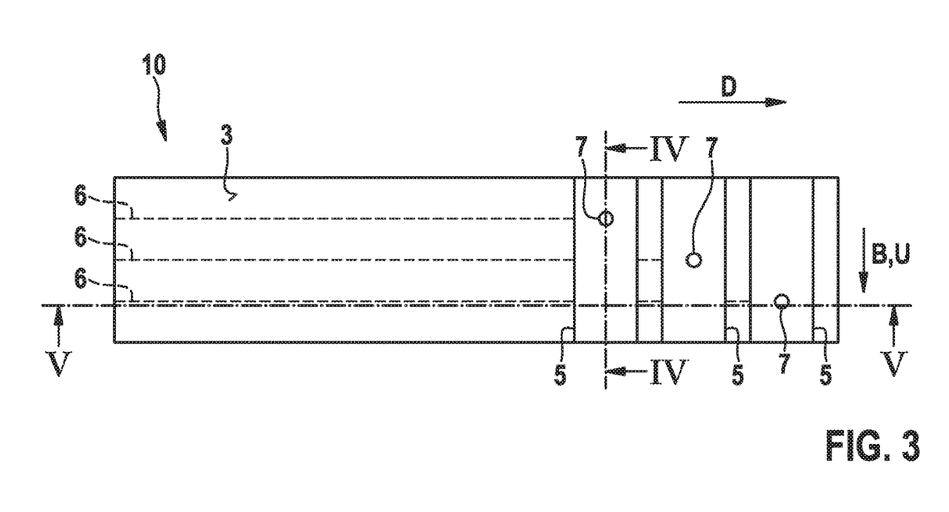
FIGS. 3-5 are a schematic representations of a sample embodiment of a sheath of the inventive electrode, wherein the sheath is shown in the form of a planar semi-finished product.
Figure 4:
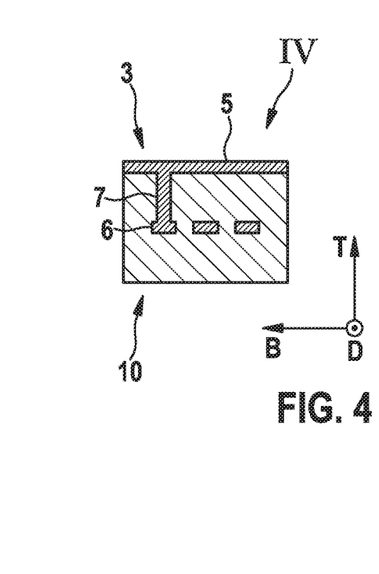
Figure 5:
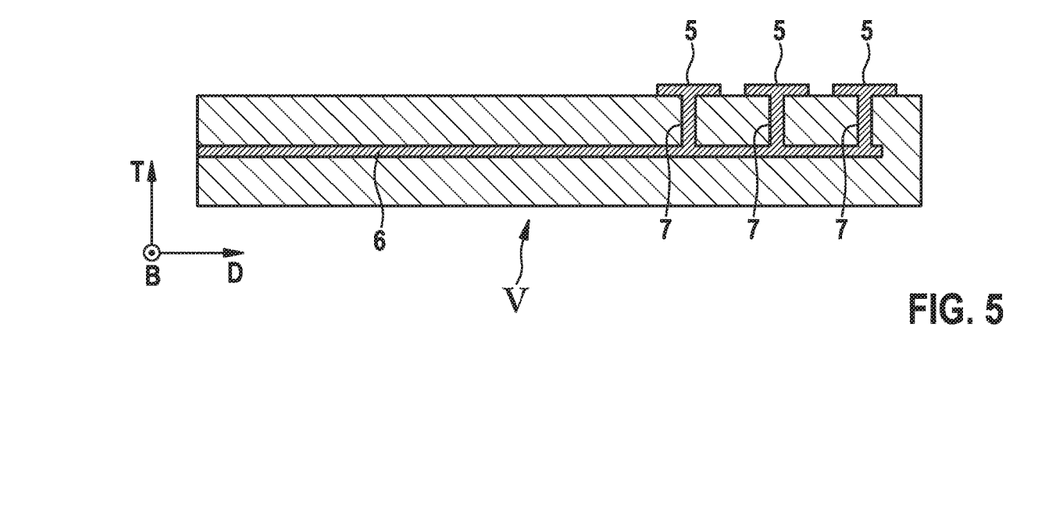

FIGS. 3-5 show a schematic top view and cross sectional views of a planar sheath in the form of a semi-finished product of another sample embodiment of the implantable electrode 1. Elements whose function and/or structure correspond to those of elements of the sample embodiments in FIGS. 1-2 are labeled using the same reference numbers. One skilled in the art will appreciate that for brevity, only the differences from the sample embodiments in FIGS. 1-2 are discussed below.

FIG. 3 shows a planar sheath 10 as a semi-finished product of the sheath 4 of the electrode 1. The outside 3 of the planar sheath 10 corresponds to the outside 3 of the sheath 4 of the electrode 1. The outside 3 of the planar sheath 10 has three strip-shaped contact elements 5 arranged on it, which are arranged one after the other and spaced apart from one another in a longitudinal direction D of the planar sheath 10, this direction corresponding to the longitudinal direction D of electrode 1. In a width direction B, which corresponds to the peripheral direction U when the planar sheath 10 is installed, the contact elements 5 can completely cover the outside 3.

Each of the contact elements 5 can have an electrically conductive connection with another connection cable 6. Thus, the planar sheath 10 can have, for example, three connection cables 6. Each of the connection cables 6 can have, with the help of another feedthrough 7, an electrically conductive connection with one of the contact elements 5.

In the sample embodiment in FIG. 3, the connection cables 6 extend only as far as the feedthrough 7, which makes the electrically conductive connection of the corresponding connection cable 6 with the respective contact element 5. However, alternatively, the connection cables 6 can also extend in the longitudinal direction D all the way behind this feedthrough 7, and even completely through the planar sheath 10. Unwanted contact of one of the connection cables 6 with another contact element 5 is prevented by the fact that the contact elements 5 are arranged on the outside 3 and the connection cables 6 are arranged separated from the outside 3 in a thickness direction T pointing transverse to the longitudinal direction D and to the width direction B.

FIG. 4 shows a schematic view of the planar sheath 10 of the sample embodiment in FIG. 3 in a section IV that extends through one of the contact elements 5, transverse to the longitudinal direction D. The longitudinal direction D points out of the plane of projection. In the width direction B, the connection cables 6 are arranged next to one another and spaced apart from one another. In the thickness direction T, the connection cables 6 are separated from the contact element 5. The feedthrough 7, which provides an electrically conductive connection of the contact element 5 that is shown with one of the connection cables 6, runs in the thickness direction T from the connection cable 6 to the contact element 5.

The connection cables 6 can be arranged on an inside of the planar sheath 10 opposite the outside 3. However, in the sample embodiment in FIG. 4, the connection cables 6 are embedded in the planar sheath 10 in such a way that contact can only be made with the connection cables 6 through one of the contact elements 5 and the respective feedthrough 7 [that runs] transverse to the longitudinal direction D.

FIG. 5 shows a sectional view of the planar sheath 10 of the sample embodiment in FIG. 3 in which the cutting plane V runs through one of the connection cables 6, that is, parallel to the longitudinal direction D and the thickness direction T.

Figure 6:
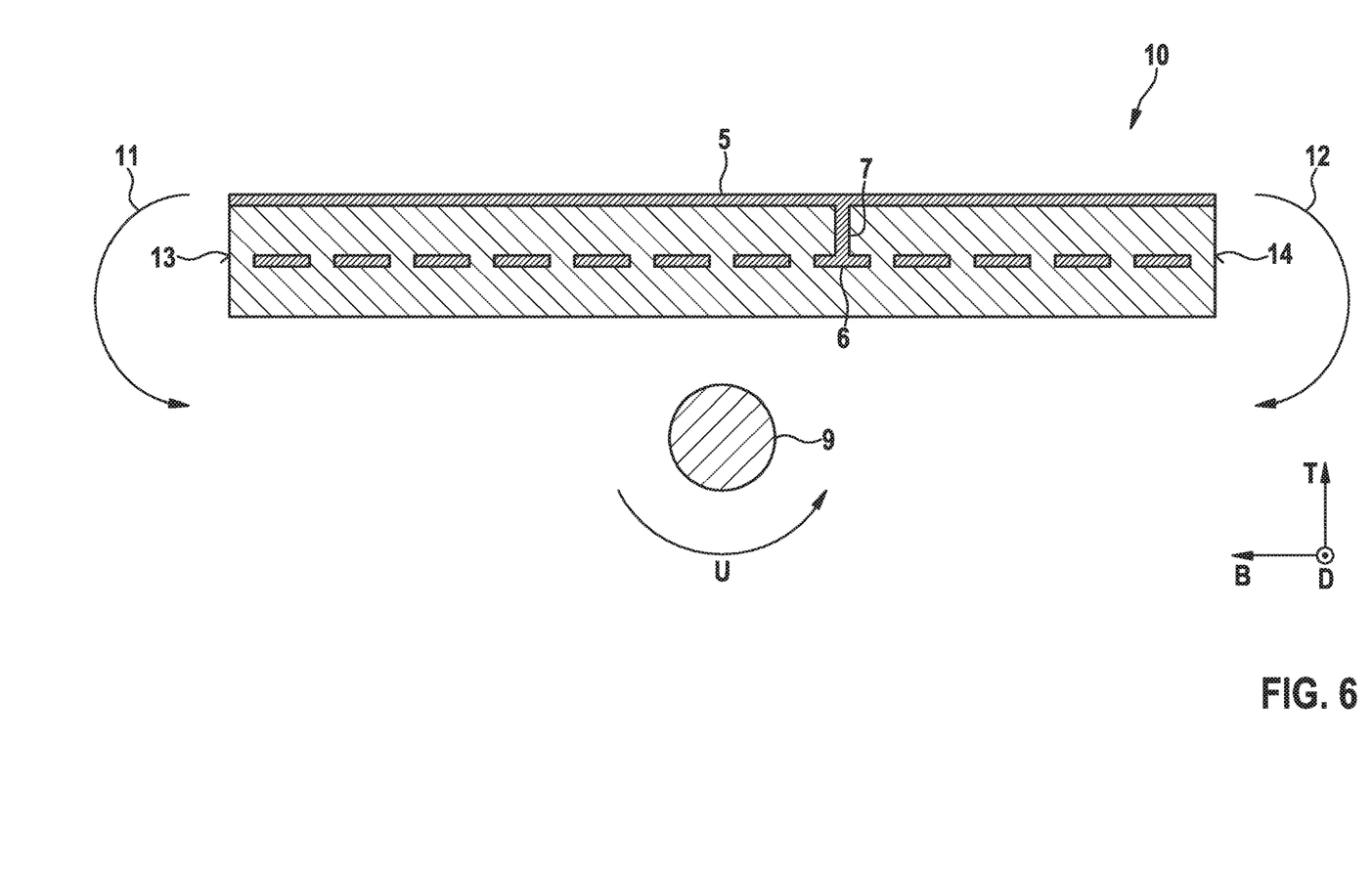
FIG. 6 is a schematic sectional view of a sample embodiment of the planar sheath with a core.

FIG. 6 shows a sectional view of another sample embodiment of the planar sheath 10. Elements whose function and/or structure correspond to those of elements of the previous sample embodiments are labeled using the same reference numbers. One skilled in the art will appreciate that for brevity, only the differences from the previous sample embodiments are discussed below.

The cutting plane runs through a contact element 5, parallel to the width direction B and the thickness direction T, comparable to FIG. 4. In the sectional view in FIG. 6, a feedthrough 7 connects one of the connection cables 6 of the planar sheath 10 with a contact element 5. The planar sheath 10 has multiple, for example, ten connection cables 6, only one of which, however, is connected by the feedthrough 7 with the contact element 5 in a way that is visible in FIG. 6. However, the planar sheath 10 can have one contact element 5 per connection cable 6, each of the contact elements 5 being able to have an electrically conductive connection through a feedthrough 7 with one of the connection cables 6. However, not only the contact elements 5, but rather also the feedthroughs 7, which electrically connect those contact elements 5 that are not shown with one of the connection cables 6, are in front of or behind the cutting plane, in and/or opposite the longitudinal direction D, so that they are not visible.

As is shown by the curved arrows 11, 12, the planar sheath 10 can be wrapped around the core 9 in such a way that the sheath 10 wraps around the core 9 in the peripheral direction U and forms the sheath 4. As an alternative to pressing the planar sheath 10 around core 9, it can be wrapped around a contact tool that is later removed, to provide the electrode 1 with a lumen extending through the electrode 1 along the longitudinal axis L. The core 9 can also have a lumen, and consequently be in the form of a hollow cylinder or tubular.

The planar sheath 10 can at least partly or even completely surround the core 9, so that its side walls 13, 14 extending parallel to the longitudinal direction D contact each other when the planar sheath 10 has been wrapped around the core 9. Alternatively, a gap can remain between the side walls 13, 14, to prevent the side walls 13, 14 from overlapping in case the planar sheath 10 might haves width tolerances.

Figure 7:
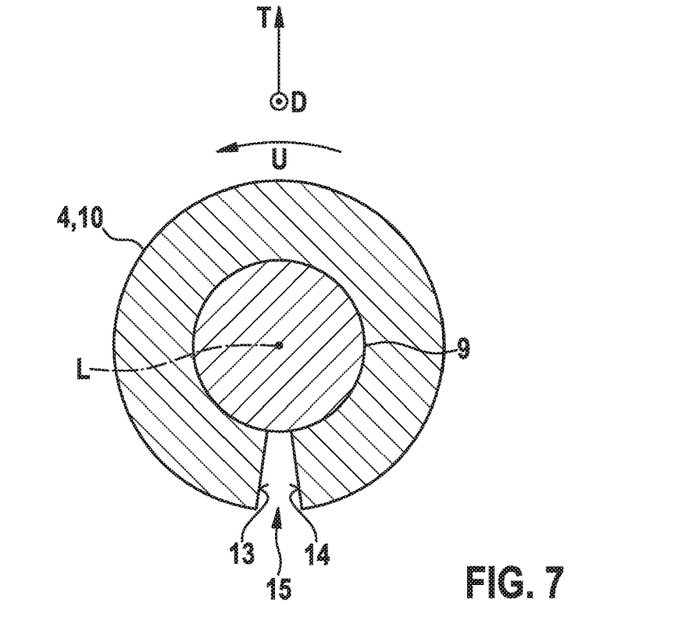
FIG. 7 is a schematic sectional view of the sheath of the sample embodiment according to FIG. 6 wrapped around the core.
Figure 8:
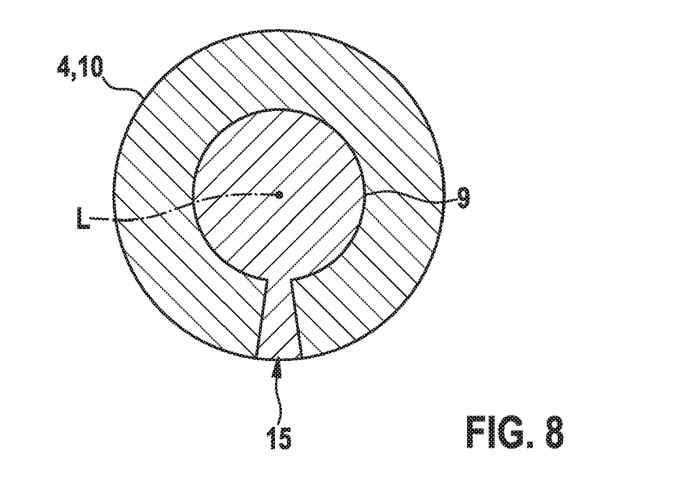
FIG. 8 is a schematic sectional view of the sample embodiment according to FIG. 7 after thermal treatment.

FIGS. 7-8 schematically show the planar sheath 10 and the core 9, for example, of the sample embodiment in FIG. 6, in the same sectional view, in which the planar sheath 10 in FIG. 7 has been wrapped around the core 9. A gap 15 remains between the side walls 13, 14, so that they are arranged spaced apart from one another in the peripheral direction U. To provide a firm connection of the sheath 10 with the core 9, the sheath 10 and the core 9 can be at least partly fused with one another.

FIG. 8 shows the sheath 10 fused with the core 9 and forming the sheath 4. If the side walls 13, 14 have contacted one another when the core 9 fused with the sheath 10, then the side walls 13, 14 can also be fused with one another. However, in the sample embodiment shown in FIG. 8, the gap 15 remains between the side walls 13, 14. After fusion of the core 9 with the planar sheath 10, the gap 15 can be filled with solidified material of the core 9 and/or solidified material of the sheath 10.

Figure 9:
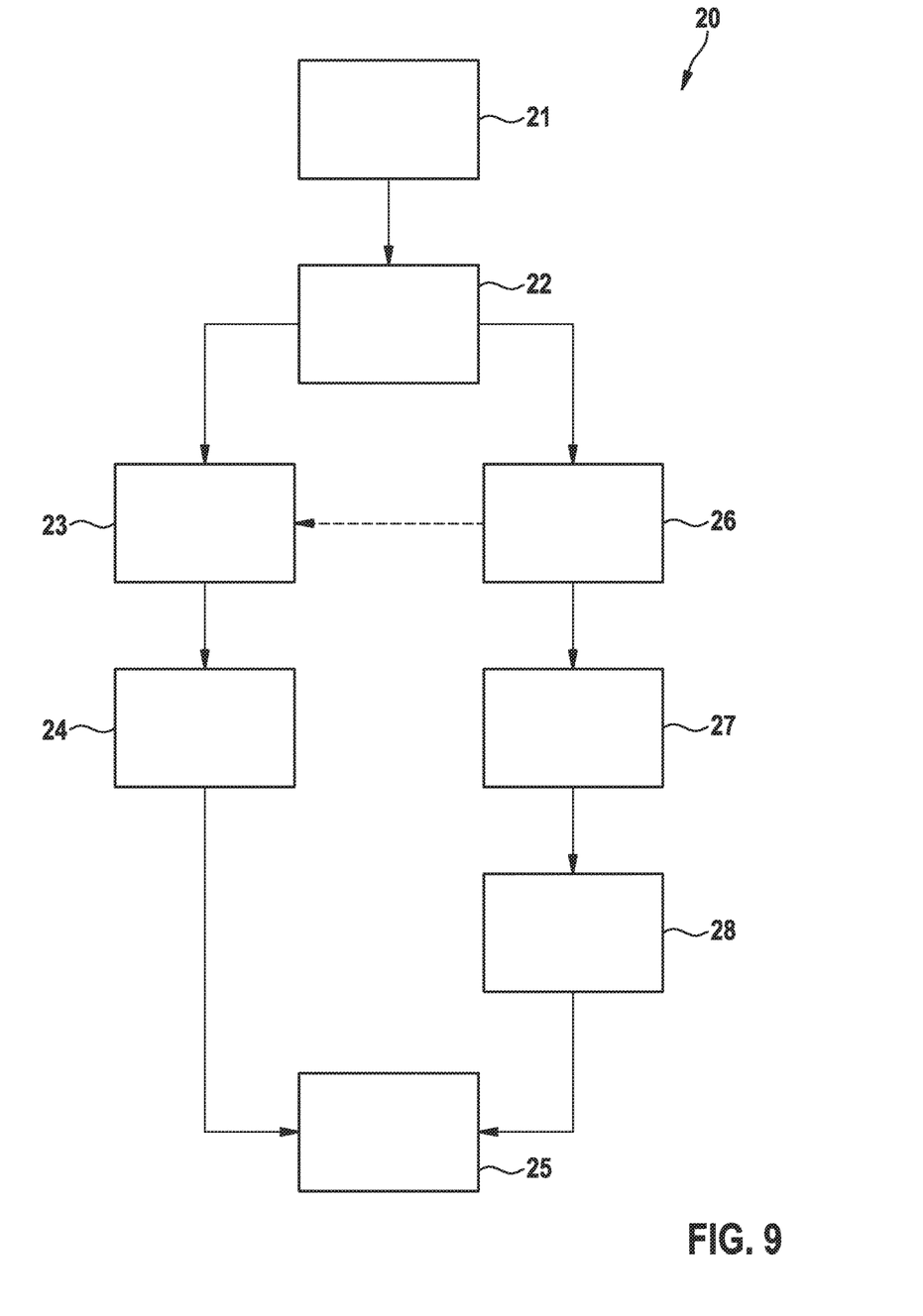
FIG. 9 is a schematic representation of a sample embodiment of the inventive process to produce the implantable electrode.

FIG. 9 shows a first sample embodiment of the inventive process for producing an implantable electrode, for example, the implantable electrode of one of the previous sample embodiments. One skilled in the art will appreciate that for simplicity, elements of the previous sample embodiments that are used to explain the process below, are labeled using the same reference numbers as in the previous description.

The process 20 starts with a first process step 21. In the first process step 21, a film at least partly forming the planar sheath 10 can be provided, for example. In order to allow an electrically conductive connection of at least one connection cable 6 with at least one contact element 5, the film can be perforated at a predetermined position in process step 21. For example, the film can be perforated mechanically, for instance, with a punch, or using a laser or a lithography apparatus.

Process step 21 is followed by process step 22, in which the contact element 5, the connection cable 6, and the feedthrough 7 connecting the contact element 5 and the connection cable 6 are formed on the film. For example, first the contact element 5 or the connection cable 6 can be additively or subtractively provided on one side of the film. Following this, the feedthrough can be made in the hole that is formed. Following this, the not yet formed contact element 5 or the not yet formed connection cable 6 can be formed on the other side of the film. The contact element 5 is formed on one side of the film and the connection cable 6 is formed on a side of the film opposite the contact element 5. The hole connects the two sides with one another.

If the implantable electrode 1 is made with a core 9, then process step 22 can be followed by process step 23, in which the planar sheath 10, that is the film provided with the contact element 5, the connection cable 6 and the feedthrough 7, is wrapped around the core 9. Process step 23 can be followed by process step 24, in which the sheath 10 is fastened to the core 9 and the sheath 10 can be fused, for example, with the core 9 top accomplish this. When this is done, the connection cable 6 can be at least partly embedded in the melting film. The process 20 ends in the then following process step 25.

Alternatively, process step 22 can be followed by process step 26. In process step 26, another film is applied to the side of the film on which the connection cable 6 is arranged. The other film can form an inside of the sheath 4, so that the connection cable 6 is not only partly embedded in the one film but, rather, completely embedded in the sheath 4, between the films.

Process step 26 can be followed by process steps 23 through 25. Alternatively, process step 26 can be followed by process step 27, in which the planar sheath 10 formed by the two films is wrapped in the form of a hollow cylindrical. For example, the sheath 10 can be wrapped around a contact tool that is later removed from the sheath 4. In the process step 28 following process step 27, the side walls 13, 14 of the planar sheath 10 wrapped in the form of a hollow cylinder can be fastened to one another, and be fused together, for example, to form the hollow cylindrical sheath 4. Process step 28 is once again followed by process step 25, in which the process ends.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMERALS

1 Implantable electrode
2 Distal end
3 Outside
4 Sheath
5 Contact element
6 Connection cable
7 Feedthrough
8 Metallic layer
9 Core
10 Planar sheath (semi-finished products)
11, 12 Arrow
13, 14 Side walls of the planar sheath
15 Gap between side walls
20 Process
21 Provide film and perforate
22 Mold contact element, connection element, and feedthrough
23 Wrap sheath around core
24 Fasten planar sheath to core
25 End
26 Apply another film
27 Wrap planar sheath in a hollow cylinder
28 Fasten side walls to one another
B Width direction
D Longitudinal direction
L Longitudinal axis
R Radial direction
T Thickness direction
U Peripheral direction

I claim:

1. An implantable electrode comprising:
a sheath extending along a longitudinal axis of the electrode, the sheath being made of an electrically insulating material; and
at least one connection cable, wherein the connection cable is at least partly embedded in the sheath and the sheath has a hollow cylindrical shape,
wherein the hollow cylindrical shape of the sheath has an inner side and an outer side,
wherein the electrode has at least one contact element, wherein the at least one contact element has a feedthrough passing through the sheath and forming an electrically conductive connection with the at least one connection cable,
wherein the at least one contact element sits on the outer side of the sheath,
wherein the at least one connection cable is arranged between two electrically insulating thermoplastic polymer films which are permanently connected with one another,
wherein a first of the two films is planar and has the at least one connection cable formed on one of its sides and the at least one contact element formed on a side of the first film opposite the at least one connection cable
wherein a second of the two films is planar and is connected to the first film on the one side of the first film where the at least one connection cable is formed.
wherein the first and second films forming the sheath are wrapped in the form of the hollow cylindrical shape, and
wherein to connect the at least one connection cable and the at least one contact element together the feedthrough is provided with a metalized opening in the one film connecting the two sides of the one film with one another.

2. The implantable electrode according to claim 1, wherein the at least one contact element extends at least partly around the longitudinal axis.

3. The implantable electrode according to claim 2, wherein the electrode has multiple contact elements.

4. The implantable electrode according to claim 3, wherein the contact elements are arranged spaced apart from one another along the longitudinal axis.

5. The implantable electrode according to claim 1, wherein the electrode has multiple connection cables that are at least partly embedded in the sheath and that are arranged spaced apart from one another in the peripheral direction of the electrode extending around the longitudinal axis.

6. The implantable electrode according to claim 1, wherein the electrode has a core against which the sheath lies.

7. The implantable electrode according to claim 6, wherein the sheath is connected with the core by material bonding.

8. The implantable electrode according to claim 6, wherein the core is made with a lumen extending continuously through the core along the longitudinal axis.

* * * * *